United States Patent [19]
Corella, II et al.

[11] Patent Number: 5,886,229
[45] Date of Patent: Mar. 23, 1999

[54] METHOD OF SYNTHESIS OF ALKALI METAL TRISUBSTITUTED BOROHYDRIDE REAGENTS

[75] Inventors: Joseph A. Corella, II, Zelienople; David H. Ellenberger, Karns City; Joerg Bruening, Allison Park, all of Pa.

[73] Assignee: Mine Safety Appliances Company, Pittsburgh, Pa.

[21] Appl. No.: 87,580

[22] Filed: May 29, 1998

[51] Int. Cl.$^6$ ....................................................... C07F 5/02
[52] U.S. Cl. .................................................... 568/1; 568/7
[58] Field of Search ............................................ 568/1, 7

[56] References Cited

U.S. PATENT DOCUMENTS

| | | |
|---|---|---|
| 2,372,671 | 4/1945 | Hansley . |
| 2,768,064 | 10/1956 | Baldridge . |
| 3,387,933 | 6/1968 | Snyder . |
| 3,617,218 | 11/1971 | Tamelen et al. ........................ 23/204 |
| 3,998,941 | 12/1976 | Nelson .................................... 423/646 |
| 4,327,071 | 4/1982 | Chiu et al. ............................... 423/646 |
| 4,808,282 | 2/1989 | Gregory . |

OTHER PUBLICATIONS

J Org Chem 46, pp. 2712–2717, 1981.
J Org Chem 52 pp. 728–730, 1987.
CA:93:35359 abs of Tetrahedron by Brown, 37(13) pp. 2359–2362, 1981.
CA:93:95308 abs of J Organomet Chem by Brown 188(1) pp. 1–10, 1980.
Bulletin Korean Chem Soc. vol. 7, No. 1 (1986) 66–69, Jin Soo Cha et al. Attempts on the Preparation of Lithium Trialkoxyborohydrides: Stability and Stereoselective Reduction of Cyclic Ketones.
Journal of Molecular Catalysis, 84 (1993) 211–221, Yiping Zhang et al. Highly Active Alkali Metal Hydrides; Their Catalytic Syntheses and Properties.
Tetrahedron Letters, vol. 29, No. 26 (1988) pp. 3195–3196, John Soderquist et al. A Simple, Efficient Method for the Purification of Potasium Hydride and Its Role in New Borohydride Chemistry.
Tetrahedron Letters, vol. 29, No. 26 (1988) pp. 3197–3200, John L. Hubbard Purification of Sodium and POtassium Hydrides; Preparation of Trialkyborohydrides With Exceptionally Large Steric Requirements.
Journal of the American Chemical Society 100:11 (1978) 3343–3349, Herbert C. Brown et al. Addition Compounds of Alkali Metal Hydrides. 15., Steric Effects in the Reaction of Representative Trialkylboranes With Lithium and Sodium Hydrides to Form the Corresponding Trialkylborohydrides.

*Primary Examiner*—Gary Geist
*Assistant Examiner*—Jean F. Vollano
*Attorney, Agent, or Firm*—James G. Uber; Henry E. Bartony, Jr.

[57] ABSTRACT

Synthetic routes for forming alkali metal substituted borohydride compounds include the step of reacting an alkali metal reagent, a hydrogen donor, and a substituted borane. The reactions proceed without the requirement of specialized handling of alkali metal hydrides associated with prior synthetic processes for the production of alkali metal trisubstituted borohydride compounds. A chemical composition comprises solid potassium tri-sec-butyl borohydride.

35 Claims, No Drawings

METHOD OF SYNTHESIS OF ALKALI METAL TRISUBSTITUTED BOROHYDRIDE REAGENTS

FIELD OF THE INVENTION

The present invention relates to a method for the synthesis of substituted borohydride reagents and, particularly, to a method for the synthesis of alkali metal trisubstituted borohydride reagents from an alkali metal, a hydrogen donor, and a trisubstituted borane.

BACKGROUND OF THE INVENTION

Since the early 1970's there has been a strong interest in synthesizing alkali metal trisubstituted borohydride reagents because of their unique reactivity and synthetic utility in organic chemistry. Alkali metal trisubstituted borohydrides reagents are used in organic synthesis primarily as regioselective and stereoselective borohydride reducing agents. To date, all preparations of alkali metal trisubstituted borohydrides have focused on the reaction of alkali metal hydrides or lithium aluminum reagents and trisubstituted boranes to produce the above mentioned compounds. The most common method of producing trisubstituted borohydrides is via the reaction of alkali metal hydrides with trisubstituted boranes as represented by the following equation wherein M represents an alkali metal:

Unfortunately, current processes for the production of trisubstituted borohydride reagents are very limited in scope and have substantial drawbacks associated therewith. For example, commercially available alkali metal hydrides (particularly, lithium and sodium hydrides) are not highly reactive in such reactions, typically requiring special washing and activating steps. Moreover, excesses of the alkali metal hydride are required is such reactions. Even with washing and activating procedures, however, certain trisubstituted borohydrides (for example, lithium tri-sec-butylborohydride) cannot be produced from commercially available alkali metal hydrides. Moreover, other special handling techniques, including hazardous material precautions, are required for alkali metal hydrides (particularly, potassium hydride). Indeed, because potassium hydride reagents are extremely difficult/hazardous to handle, there are no industrial organic processes incorporating such reagents into their synthetic schemes. Furthermore, current procedures for commercial synthesis of alkali metal hydride reagents require relatively high pressures and high temperatures.

It is desirable to develop methods of producing alkali metal substituted borohydride reagents that lessen or eliminate the above drawbacks.

SUMMARY OF THE INVENTION

The present invention provides synthetic routes for forming alkali metal trisubstituted borohydride compounds from an alkali metal reagent, a hydrogen donor, and a trisubstituted borane. The reactions of the present invention proceed without the requirement of special handling techniques associated with alkali metal hydride reactants. Although alkali metal hydrides may be intermediates in the reactions of the present invention, there is no need to isolate or handle such alkali metal hydrides. Indeed, the reactions of the present invention may occur in a single reaction vessel. Furthermore, the reactions of the present invention proceed at relatively low pressures and temperatures. For example, the pressure of the present reaction is preferably no greater than approximately 100 psig. More preferably, the reaction pressure is no greater than approximately 50 psig.

The alkali metal trisubstituted borohydride products of the present invention can be represented by the general formula $M[R^1R^2R^3B]H$, wherein M represents the alkali metal and $R^1$, $R^2$ and $R^3$ are preferably, independently, an alkyl group, an aryl group, an aryloxyl group, an alkoxyl group or an amino group. The trisubstituted borane reagents of the present invention can be represented by the formula $R^1R^2R^3B$, wherein $R^1$, $R^2$ and $R^3$ are as defined above. A wide variety of trisubstituted boranes, including, for example, tri-sec-butylborane, tricyclohexylborane, triethylborane, triphenylborane, (S)-B-isopinocampheyl-9-borabicyclo[3.3.1]nonane, trisiamylborane, triisopropyl borate, and 9-isopropoxy-9-borabicyclo[3.3.1]nonane have been reacted in the present invention. Alkali metals suitable for use in the present invention include potassium (K), lithium (Li), sodium (Na) and cesium (Cs).

As used herein, the term "alkyl group" refers preferably to $C_1$–$C_{12}$ alkyl groups and, more preferably, to $C_2$–$C_{12}$ alkyl groups. The alkyl groups can be normal, branched or cyclic. As used herein, the term "aryl group" refers preferably to phenyl and napthyl groups. As used herein, the term "alkoxyl group" refers preferably to groups having the formula —$OR^4$, wherein $R^4$ is preferably an alkyl group as defined above. As used herein, the term "aryloxyl group" refers preferably to groups having the formula —$OR^5$, wherein $R^5$ is preferably an aryl group as defined above. As used herein, the term "amino group" refers preferably to groups having the formula —$NR^6R^7$, wherein $R^6$ and $R^7$ are, independently, hydrogen, an alkyl group, an aryl group, or a trialkylsilyl group. As used herein, the term "tialkylsilyl group" preferably refers to a group having the formula —$SiR^8R^9R^{10}$, wherein each of $R^8$, $R^9$, and $R^{10}$ are preferably, independently, an alkyl group as defined above.

The various alkyl, aryl, alkoxyl, aryloxyl and amino groups discussed above can be substituted or unsubstituted. If substituted, such groups are preferably substituted with unreactive substituents. In that regard, the substituent groups are preferably compatible with the borohydride materials. Because of the reactive nature of the borohydride materials, such substituents are somewhat limited and typically include alkyl groups, aryl groups, alkoxyl groups, aryloxyl groups, arylthio groups, dialkylamino groups, diarylamino groups, dialkylphosphino groups and diarylphosphino groups. See U.S. Pat. No. 4,082,810 for a discussion of such groups.

As used herein, the term "hydrogen donor" refers to a chemical entity suitable to provide a source of hydrogen (or an isotope of hydrogen, that is, deuterium or tritium) in the reactions of the present invention. Preferred hydrogen donors for use in the present invention include, but are not limited to, hydrogen, deuterium, tritium, ethers, cyclohexadiene, and cyclohexene.

In one embodiment of the present invention, the alkali metal trisubstituted borohydride is synthesized by reacting an alkali metal in a solvent with a hydrogen donor in the presence of the corresponding trisubstituted borane. As used herein, the term "solvent" refers to a liquid reaction matrix used to disperse the alkali metal reactant, to dissolve a catalyst in the case that a catalyst is used, as a solvent matrix for the product, and/or as a hydrogen donor for the reaction. Thus, the present invention provides a method of synthesizing a alkali metal trisubstituted borohydride compound having the formula $M[R^1R^2R^3B]H$, wherein M is K, Li, Na or Cs, and $R^1$, $R^2$ and $R^3$ are, independently, an alkyl group, an aryl group or an alkoxyl group, comprising the step of reacting an alkali metal, a hydrogen donor (preferably hydrogen gas), and a trisubstituted borane having the formula $R^1R^2R^3B$ in a single reaction vessel to produce the trisubstituted borohydride compound. This reaction can be represented as follows:

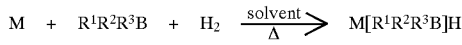

A number of trisubstituted boranes and alkali metal trisubstituted borohydride compounds can begin to isomerize, break down or thermally degrade at elevated temperatures. The trisubstituted borane substrates and the alkali metal trisubstituted borohydride compound products of the present invention are, therefore, preferably sufficiently thermally stable at temperatures experienced during the reaction of the present invention such that they do not completely thermally degrade. Preferably, the trisubstituted boranes and alkali metal trisubstituted borohydride compounds of the present invention are sufficiently thermally stable such that little or no thermal degradation occurs during the reaction. As clear to one skilled in the art, such degradation reduces the efficiency of the reaction. Moreover, byproducts resulting from thermal degradation of the trisubstituted boranes and alkali metal trisubstituted borohydride compounds can be difficult to separate from the desired product.

In the case of potassium, it has surprisingly been discovered that many trisubstituted boranes can be converted to the corresponding potassium trisubstituted borohydride in a commercially reasonable time at relatively low reaction pressures without the use of a catalyst. For example, tri-sec-butylborane, tricyclohexylborane, triethylborane, triphenylborane, (S)-B-isopinocampheyl-9-borabicyclo[3.3.1]nonane, and 9-isopropoxy-9-borabicyclo[3.3.1]nonane (9-isopropoxy-9-BBN) have all been converted to the corresponding potassium trisubstituted borohydride in the reaction of the present invention without the use of a catalyst.

Other potassium trisubstituted borohydrides, as well as lithium, sodium and cesium trisubstituted borohydrides, can be synthesized by reacting the alkali metal in a solvent with a hydrogen donor in the presence of the corresponding trisubstituted borane and an appropriate hydrogenation catalyst or catalysts. The hydrogenation catalysts are preferably transition metal salts (for example, $FeCl_3$) and/or polycyclic aromatic compounds (for example, napthalene and/or phenanthrene). Such reactions can be represented by the following general formula:

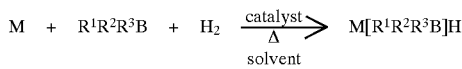

Preferred catalysts and catalyst systems for use with potassium metal include phenanthrene, triphenylene, napthalene plus a transition metal (for example, $FeCl_3$, $Ti(OiPr)_4$ and $TiCl_4$), and alkalimetal aluminum dihydrocarbon dihydride in aromatic solvents. Preferred catalysts and catalyst systems for use with sodium metal include napthalene, napthalene plus a transition metal (for example, $FeCl_3$, $Ti(OiPr)_4$ and $TiCl_4$), and alkalimetal aluminum dihydrocarbon dihydride in aromatic solvents. Preferred catalysts and catalyst systems for use with lithium metal include $FeCl_3$, napthalene plus a transition metal (for example, $FeCl_3$, and $Ti(OiPr)_4$), triphenylene plus a transition metal halide, and alkalimetal aluminum dihydrocarbon dihydride in aromatic solvents.

In another embodiment, the present invention provides a method for synthesizing an alkali metal trisubstituted borohydride compound having the formula $M[R^1R^2R^3B]H$, wherein M is K, Li, Na or Cs, and $R^1$, $R^2$ and $R^3$ are, independently, an alkyl group, an aryl group, an alkoxyl group, an aryloxyl group or an amino group, comprising the steps of:
 a. reacting an alkali metal M with a hydrogen donor; and
 b. combining a reaction mixture of step a. with a trisubstituted borane having the formula $R^1R^2R^3B$.

The above reaction scheme can be represented by the following general formula:

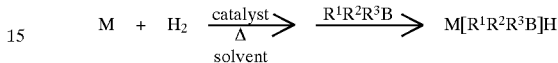

Preferably, the alkali metal is reacted with a hydrogen donor in the presence of a hydrogenation catalyst or catalysts (for example, a transition metal salt and/or a polycyclic aromatic compound).

In the reactions of the present invention, the alkali metal can be introduced into the reaction mixture in a number of forms. For example, in one embodiment of the present invention the alkali metal is preferably present in the reaction mixture as a liquid. In that regard, the reaction may take place above the melting temperature of the alkali metal. Preferably, a dispersion of the liquid alkali metal is created in a solvent by providing sufficient agitation.

Potassium metal, for example, has a melting point of approximately 63° C. Preferably, therefore, the reaction temperature is at or above approximately 63° C. As discussed above, however, some alkali metal trisubstituted borohydrides undergo thermal degradation at elevated temperatures. Therefore, in the case of a reaction involving molten potassium metal, the reaction temperature is preferably maintained between approximately 63° C. and approximately 120° C. Moreover preferably, the reaction temperature is maintained between approximately 70° C. and approximately 100° C.

The alkali metals can also be reacted at temperatures below their melting points. Potassium, for example, forms a eutectic sodium-potassium alloy (NaK). The NaK alloy remains a liquid even at temperatures below 0° C., enabling a relatively fine dispersion of the metal reactant in the liquid reaction matrix. Use of such a source of the alkali metal potassium enables reaction temperatures below the melting point of potassium metal in certain reactions of the present invention, thereby decreasing the likelihood of thermal degradation of the product.

Solid alkali metals are also suitable for use in the present invention. Preferably, such solid alkali metals have a relatively high surface area to enhance reaction rate. For example, a dispersed solid alkali metal may be combined with a substrate such as graphite (for example, an intercalation compound). In certain cases, powders of alkali metals can also be used.

The synthetic schemes of the present invention provide the first commercially acceptable processes for producing alkali metal trisubstituted borohydrides. The present inventors are the first to demonstrate the reactivity of an alkali metal, a hydrogen donor, and trisubstituted borane to produce the corresponding alkali metal trisubstituted borohydride. Further, virtually any aromatic, aliphatic, or etheral solvent can be used in the method of the present invention, whereas only etheral solvents such as tetrahydrofuran (THF) were used in prior methods.

Moreover, the present invention also provides a method for the formation, isolation, and characterization of solid potassium trisecbutyl borohydride (K[(sec-Bu)$_3$B]H or KTSBB). This result is enabled by the wide range of solvents suitable for use in the reactions of the present invention. In that regard, the reactions set forth above are preferably carried out in nonpolar solvents to produce solid potassium trisecbutyl borohydride. Such nonpolar solvents include alkanes. Preferably, such alkanes are $C_1$–$C_{12}$ alkanes. Previously, potassium tri-sec-butyl borohydride could only be formed and characterized in solution. The present inventors are thus the first to isolate and characterize solid potassium trisecbutyl borohydride.

Isolation of solid potassium trisecbutyl borohydride enables one to, for example, create solutions of potassium trisecbutyl borohydride that were heretofore impossible. For example, solutions of potassium trisecbutyl borohydride in solvents which are incompatible with the reactants (for example, with potassium metal, potassium hydride and/or trisecbutyl borane) used to produce potassium trisecbutyl borohydride are made possible. Such solvents include, for example, methylene chloride and chloroform.

DETAILED DESCRIPTION OF THE INVENTION

The present invention provides processes for commercial/industrial production of alkali metal trisubstituted borohydride reagents via the reaction of an alkali metal, a hydrogen donor (preferably hydrogen gas) and a trisubstituted borane. Unlike the present invention, all prior methods for the production of alkali metal trisubstituted borohydrides require isolation and special handling of alkali metal hydride reagents.

"ONE-STEP" SYNTHESIS

In one embodiment, the present invention provides a single-step, single-reactor synthetic scheme in which the alkali metal, a hydrogen donor, a solvent and the trisubstituted borane are charged to a reaction vessel. In a model reaction, potassium was reacted with hydrogen gas and tri-sec-butyl borane (TSBB) to form potassium tri-sec-butylborohydride as represented in the following equation:

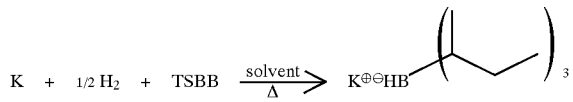

$$K + 1/2\, H_2 + TSBB \xrightarrow[\Delta]{solvent} K^{\oplus \ominus}HB\!\left(\!\!\diagup\!\!\diagdown\right)_{\!3}$$

In the case of potassium metal and tri-sec-butylborane, it was found that the reaction would proceed to form potassium tri-sec-butylborohydride even in the absence of a catalyst. A study of the reaction progress for that reaction at 85° C., with THF as a solvent, and under an H$_2$ atmosphere of with a reaction pressure of approximately 50 psig is provided in FIG. 1. A study of the effects of several catalysts upon the reaction is provided in Table 1.

TABLE 1

| Catalyst [g] | K-metal [mol] | TSBB [mol] | Temperature [°C.] | Yield |
|---|---|---|---|---|
| none | .424 | .354 | 85 | 94% |
| none | .393 | .403 | 85 | 89% |
| none | 0.354 1.7% | 0.348 | 85 | 88% |

TABLE 1-continued

| Catalyst [g] | K-metal [mol] | TSBB [mol] | Temperature [°C.] | Yield |
|---|---|---|---|---|
| 0.71 napthalene | 0.348 | 0.346 | 85 | — |
| 1 graphite | 0.348 | 0.34 | 85 | 62% |
| 1 phenanthrene 1.60 mol % | 0.3499 | 0.385 | 85 | 81% |
| 0.25 phenanthrene 0.4 mol % | 0.348 | 0.34 | 75 | 84% |
| 0.5 phenanthrene 0.8 mol % | 0.348 | 0.34 | 75 | 92% |
| 0.5 phenanthrene 1.6 mol % | 0.174 | 0.17 | 75 | 87% |

In Table 1, the yield is defined as the amount of potassium trisecbutyl borohydride divided by the total amount of boron compounds (as determined by $^{11}$B-NMR), multiplied by 100%. As seen from the experiments with no catalyst in Table 1, the reaction can proceed to a yield of at least 94% in the absence of a catalyst.

These reactions can proceed in a wide variety of solvents as illustrated in Table 2.

TABLE 2

| K-metal [mol] eq | TSBB [mol] | Solvent | Temp. [°C.] | H$_2$ [psig] | % KTSBBH of total B via $^{11}$B-NMR (Yield) |
|---|---|---|---|---|---|
| 0.484 1.2 | 0.403 | Dimethoxyethane (Monoglyme) | 84–90 | 50 | 90 |
| 0.42 1.2 | 0.35 | Dimethoxyethane (monoglyme) | 86 | 0 (41 psig N$_2$) | 78 |
| 0.484 1.2 | 0.403 | Toluene | 84 | 50 | 75 |
| 0.4243 1.2 | 0.353 7 | THF | 83 | 50 | 94 |

In the second example of Table 2, no hydrogen gas was supplied to the reaction vessel. In this reaction, dimethoxyethane acted as a hydrogen donor.

In addition to tri-sec-butylborane, other substrates were found to react with potassium under a hydrogen atmosphere without addition of a hydrogenation catalyst to produce the corresponding potassium trisubstituted borohydride. Several such experiments are summarized in Table 3A.

TABLE 3A

| Borane | Yield [ca. %] (based on $^{11}$B-NMR) |
|---|---|
| B(sec-butyl)$_3$ | 88–94 |
| BEt$_3$ | 42 |
| B(cyclohexyl)$_3$ | 71 |
| BPh$_3$ | 50 |
| (S)-B-isopinocampheyl-9-borabicyclo[3.3.1]nonane | 48 |
| 9-i-Propoxy-9-BBN | 85 |
| B(O-iPr)$_3$ | 16 |

Although the mechanism of such reactions is not understood completely, it is possible that the trisubstituted borane reagent acts to catalyze the reaction of potassium with hydrogen to form a highly reactive potassium hydride intermediate. Table 3B sets forth the chemical structures of several of the trisubstituted boranes reacted in the present studies.

TABLE 3B

| Compound Name | Structure |
| --- | --- |
| Triethylborane | B(CH₂CH₃)₃ |
| Tri-sec-butylborane | 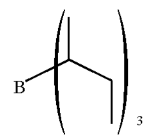 |
| Tricyclohexylborane | 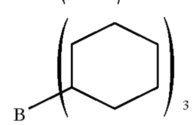 |
| Triphenylborane | B(C₆H₅)₃ |
| (S)-B-Isopinocampheyl-9-borabicyclo [3.3.1] nonane | 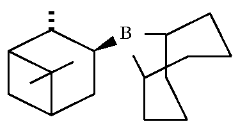 |
| Trisiamylborane | 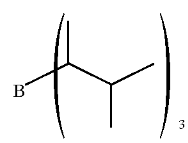 |
| Triisopropyl borate | 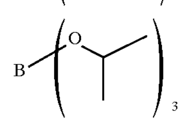 |
| 9-Isopropoxy-9-borabicyclo [3.3.1] nonane | 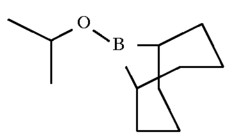 |

As seen from the several studies summarized in Table 4, a variety of sources of potassium metal can be used in the present reactions. In several experiments, a sodium potassium alloy (NaK) was used in the reaction with very good results. Only the potassium portion of the alloy was found to react with the tri-sec-butylborane substrate of these studies. In the absence of a hydrogenation catalyst, the sodium was found to not appreciably react with tri-sec-butylborane in a hydrogen atmosphere whether introduced as a NaK metal alloy, as sodium metal with potassium metal, or as sodium metal without potassium metal.

TABLE 4

| Metal [mol] (eq) | TSBB [mol] | Temp [°C.] | % KTSBBH of total B compounds via ¹¹B-NMR (Yield) |
| --- | --- | --- | --- |
| NaK [0.2 Na] [0.43 K] | 0.359 | 85 | 95 |
| NaK [0.0951 Na] [0.2 K] | 0.3 | 85 | 57 |
| K + Na | 0.256 | 84 | 81.6 |

TABLE 4-continued

| Metal [mol] (eq) | TSBB [mol] | Temp [°C.] | % KTSBBH of total B compounds via ¹¹B-NMR (Yield) |
| --- | --- | --- | --- |
| 0.3069 K (1.2 eq) 0.0035 Na | | | |
| NaK [0.19 Na] [0.396 K] | 0.329 | 42 | 69 |

In addition to the potassium metal reactions discussed above, which proceeded without a catalyst, a broad range of potassium trisubstituted borohydrides, as well as a broad range of lithium trisubstituted borohydrides, sodium trisubstituted borohydrides and cesium trisubstituted borohydrides can be formed in the one-step, single-vessel reaction of the present invention with the use of a hydrogenation catalyst. Moreover, even in those reactions with a potassium metal reagent that can proceed without a catalyst, use of a catalyst therein may decrease reaction time (that is, increase reaction rate). A detailed study of the effects of catalysts upon reaction rates in the present reaction has not yet been undertaken. Those hydrogenation catalysts suitable to catalyze the reaction of the alkali metal with hydrogen to form the corresponding alkali metal hydride are preferred in the reaction of the present invention.

In one experiment, lithium metal powder was reacted with tri-sec-butylborane in a hydrogen atmosphere (50 psig, at 85° C.) in the presence of 2 mol % $FeCl_3$, giving lithium tri-sec-butylborohydride. This product could not be formed in the absence of a hydrogenation catalyst. Moreover, this product cannot be synthesized from commercially available lithium hydride.

"TWO-STEP" SYNTHESIS

In another embodiment of the present invention, the alkali metal and a hydrogen donor (preferably, hydrogen gas) are first added to the reactor and heated in the presence of a solvent. Preferably, a hydrogenation catalyst is also present in the reactor. In a second step, the trisubstituted borane is then added to the reaction mixture. Substantially quantitative yields of the alkali metal trisubstitued borohydrides were obtained in this reaction scheme. Several experiments illustrating a model reaction with a potassium tri-sec-butylborane reagent and a number of catalysts are summarized in Table 5 below.

TABLE 5

| Catalyst | % KTSBBH of total via ¹¹B-NMR |
| --- | --- |
| phenanthrene | 96.5 |
| butene | — |
| none | 29 |
| none | 18 |
| triphenylene | 87 |
| pyrene | 24 |
| napthalene | 24 |

In the experiments of Table 5, potassium metal (13.68 g, 0.35 mol), THF (241.6 g) and the indicated catalyst (if any) were placed in a Parr pressure reactor. The reactor was reassembled and connected to a vent line and a hydrogen tank. The reaction mixture was heated to approximately 85° C., pressurized with hydrogen to approximately 50 psig and then stirred overnight. The following day, the reaction mixture was cooled to room temperature and tri-sec-butylborane (65.35 g, 0.359 mol) was added to the reaction mixture. A reaction was allowed to proceed at approximately 18° to 26° C. for approximately one hour. The resultant solution was filtered through a medium glass filter and analyzed by active hydrogen and $^{11}$B-NMR.

Using a similar experimental procedure as described above with a phenanthrene catalyst (1.6 mol %), several different substrates were studied. Three of these experiments are summarized in Table 6.

TABLE 6

| Substrate | % KBR$_3$H of total via $^{11}$B-NMR |
|---|---|
| tri-sec-butylborane | 96.5% |
| tri-ethylborane | 90% |
| tri-isopropylborate | 90% |

Once again using a similar experimental procedure as described for the experiments of Table 5 with a phenanthrene catalyst (1.6 mol %) and a tri-sec-butylborane substrate, several different solvents were studied. Three of these experiments are summarized in Table 7.

TABLE 7

| Solvent | % KTSBBH of total via $^{11}$B -NMR |
|---|---|
| THF | 96.5% |
| octane | 91% (solid KTSBBH isolated) |
| heptane | 95% (solid KTSBBH isolated) |

As evidenced from the results of Table 7, use of nonpolar solvents (for example, alkanes) in either the one-step reaction sequence or the two-step reaction sequence of the present invention enables the isolation of solid tri-sec-butylborohydride. The present inventors are the first to isolate solid tri-sec-butylborohydride. The isolation of solid tri-sec-butylborohydride ($C_{12}H_{28}BK$, $M_w$=222.25 g/mol) in the present studies was confirmed by elemental analysis performed by Galbraith® Laboratories, Inc. of Knoxville, Tenn. Two such analytical runs are summarized in Table 8 below.

TABLE 8

|  | C | H | B | K | Total |
|---|---|---|---|---|---|
| g/mol KTSBBH | 144.13 | 28.22 | 10.81 | 39.09 | 222.252 |
| wt % theory | 64.85 | 12.70 | 4.86 | 17.59 | 99.99 |
| wt % calc. Run 1 | 61.28 | 12.26 | 5.88 | 16.48 | 95.9 |
| wt % calc. Run 2 | 63.37 | 12.96 | 5.36 | 17.06 | 98.75 |

ION EXCHANGE

Trisubstituted alkali metal derivatives can also be synthesized via ion exchange (metathesis) under the present invention. Metathesis has previously been use to convert only certain potassium trialkoxyborohydrides (such as potassium triisopropoxyborohydride) to the corresponding lithium trialkoxyborohydride. See, Cha, J.S. et al., "Attempts on the Preparation of Lithium Trialkoxyborohydrides: Stability and Stereoselective Reduction of Cyclic Ketones," Bull. Korean Chem. Soc., 7(1), 66–69 (1986).

The present inventors have discovered that metathesis is also suitable to for use with alkali metal trialkylborohydrides and alkali metal triarylborohydrides. In such a metathesis reaction, a salt of the desired alkali metal (for example, lithium chloride) is reacted with the existing alkali metal trisubstituted borohydride (for example, a potassium trisubstituted borohydride or a sodium trisubstituted borohydride) to effect an ion exchange reaction.

Preferably, the salt of the desired alkali metal is more soluble in the solvent used than is the corresponding salt of alkali metal in the existing trisubstituted borohydride compound. For example, lithium trisecbutyl borohydride was formed from potassium trisecbutyl borohydride in THF via a metathesis reaction of the potassium trisecbutyl borohydride with LiCl. Because of its limited solubility in THF, KCl precipitated out of solution, driving the metathesis reaction toward completion. In a similar reaction, lithium trisecbutyl borohydride was formed from sodium trisecbutyl borohydride in THF via a metathesis reaction of the sodium trisecbutyl borohydride with LiCl.

The details of several experiments of the present invention are provided in the following Experimental Examples.

EXPERIMENTAL EXAMPLES

Example 1

Potassium tri-sec-butylborohydride in THF (2-Steps, 1-reaction vessel)

13.7 g Potassium metal, 241.7 g dry tetrahydrofuran and 1.0 g phenanthrene were charged to a Parr pressure reactor equipped with a backpressure regulator (set at 95 psig) and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained for approximately 8 hours. The reactor was cooled to approximately 25° C. and depressurized. Then 65.4 g tri-sec-butylborane was added, keeping the reaction temperature below 30° C. After completion of the addition of tri-sec-butylborane, the reaction mixture was stirred for approximately one hour and then filtered through a filter. The filtrate contained the potassium tri-sec-butyl borohydride in almost quantitative yield and >95% purity by $^{11}$B-NMR.

Example 2

Potassium tri-sec-butylborohydride in THF (2-Steps, 1-reaction vessel)

23.46 g Potassium metal, 136.64 g dry tetrahydrofuran and 1.71 g phenanthrene were charged to a Parr pressure reactor equipped with a backpressure regulator (set at 95 psig) and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained for approximately 8 hours. The reactor was cooled to 25° C. and depressurized. Then 111.48 g tri-sec-butylborane was added, keeping the reaction temperature below 30° C. After completion of the addition of tri-sec-butylborane, the reaction mixture was stirred for approximately one hour and then filtered through a filter. The filtrate contained the potassium tri-sec-butyl borohydride in almost quantitative yield and >98% purity by $^{11}$B-NMR.

Example 3

Potassium tri-sec-butylborohydride in THF (1-Step, 1-reaction vessel)

16.4 g Potassium metal, 265.0 g dry tetrahydrofuran and 64.4 g tri-sec-butylborane were charged to a Parr pressure reactor equipped with a backpressure regulator (set at 95 psig) and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained overnight. The reactor was cooled to approximately 25° C. and depressurized and the reactor content filtered through a filter. The filtrate contained the potassium tri-sec-butyl borohydride in 95% yield.

Example 4a
Potassium tri-sec-butylborohydride in THF (1-Step, 1-reaction vessel, NaK)

21.73 g Sodium-Potassium alloy (78% K, 22% Na), 241.76 g dry tetrahydrofuran and 65.35 g tri-sec-butylborane were charged to a Parr pressure reactor equipped with a backpressure regulator (set at 95 psig) and a bubbler system. The mixture was heated to 85° C.

Hydrogen gas pressure was applied to the reactor until the reactor pressure reached 50 psig. This pressure was maintained overnight. The reactor was cooled to approximately 25° C. and depressurized and the reactor content filtered through a filter. The filtrate contained the potassium tri-sec-butyl borohydride >94% purity by $^{11}$B-NMR. Less than 1% sodium tri-sec-butylborohydride was produced.

Example 4b
Potassium tri-sec-butylborohydride in THF (2-Steps, 1-reaction vessel, no catalyst)

13.68 g Potassium metal, 219.65 g dry tetrahydrofuran were charged to a Parr pressure reactor equipped with a backpressure regulator (set at 95 psig) and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained overnight. The reactor was cooled to approximately 70° C. and then 40 g tri-sec-butylborane was added. After completion of the addition of tri-sec-butylborane, the reaction mixture was stirred for approximately one hour, cooled to approximately 25° C. and then filtered through a filter. The filtrate contained the potassium tri-sec-butyl borohydride in approximately 18% yield.

Example 4c
Potassium tri-sec-butylborohydride in THF (1-Step, 1-reaction vessel, no hydrogen)

13.96 g Potassium metal, 241.76 g dry tetrahydrofuran and 63.76 g tri-sec-butylborane were charged to a Parr pressure reactor equipped with a backpressure regulator (set at 95 psig) and a bubbler system. The mixture was heated to approximately 65° C. to melt the potassium metal and then agitated to disperse the potassium metal in the tetrahydrofuran. The temperature was increased to 85° C. and the reaction mixture stirred overnight under a nitrogen atmosphere. The reactor was cooled to approximately 25° C. and depressurized and the reactor content filtered through a filter. The filtrate contained the potassium tri-sec-butyl borohydride in >74% purity by $^{11}$B-NMR.

Example 5
Potassium tri-sec-butylborohydride in Toluene 16.4 g Potassium metal, 265.0 g dry tetrahydrofuran and 64.4 g tri-sec-butylborane were charged to a Parr pressure reactor equipped with a backpressure regulator (set at 95 psig) and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained overnight. The reactor was cooled to approximately 25° C. and depressurized and the reactor content filtered through a filter. The filtrate contained the potassium tri-sec-butyl borohydride in 95% yield.

Example 6a
Potassium tri-sec-butylborohydride in Dimethoxyethane 18.9 g Potassium metal, 276.3 g dry dimethoxyethane and 73.4 g tri-sec-butylborane were charged to a Parr pressure reactor equipped with a backpressure regulator (set at 95 psig) and a bubbler system. The mixture was heated to approximately 65° C. to melt the potassium metal and then agitated to disperse the potassium metal in the dimethoxyethane. The temperature was increased to 85° C.

Hydrogen gas pressure was applied to the reactor until the reactor pressure reached 50 psig. This pressure was maintained overnight. The reactor was cooled to approximately 25° C. and depressurized and the reactor content filtered through a filter. The filtrate contained the potassium tri-sec-butyl borohydride in >91% yield.

Example 6b
Potassium tri-sec-butylborohydride in Dimethoxyethane (1-Step, 1-reaction vessel, no hydrogen)

16.42 g Potassium metal, 234 g dry dimethoxyethane and 63.76 g tri-sec-butylborane were charged to a Parr pressure reactor equipped with a backpressure regulator (set at 95 psig) and a bubbler system. The mixture was heated to approximately 65° C. to melt the potassium metal and then agitated to disperse the potassium metal in the dimethoxyethane. The temperature was increased to 85° C. and the mixture stirred overnight under a nitrogen atmosphere.

The reactor was cooled to approximately 25° C., depressurized and the reactor content filtered through a filter. The filtrate contained the potassium tri-sec-butyl borohydride in approximately 76% purity by $^{11}$B-NMR.

Example 7
Potassium B-isopropoxy-9-boratabicyclo-[3.3.1]nonane 6.39 g Potassium metal, 24.53 g B-isopropoxy-9-borabicyclo[3.3.1]nonane and 177 g tetrahydrofuran were charged to a Parr pressure reactor equipped with a backpressure regulator set at 95 psig. The mixture was heated to approximately 65° C. to melt the potassium metal and then agitated to disperse the potassium metal in the THF. The reaction temperature was increased to 85° C. and mixture stirred overnight under 50 psig of $H_2$ pressure. The reactor was cooled to room temperature and depressurized. The obtained crude material was filtered yielding a clear, water white to light tan colored solution of potassium B-isopropoxy-9-boratabicyclo[3.3.1]nonane in THF (85+% pure by $^{11}$B-NMR).

Example 8
Potassium tricyclohexylborohydride in THF 2.62 g Potassium metal, 176 g dry tetrahydrofuran and 17.8 g tricyclohexylborane were charged to a Parr pressure reactor equipped with a backpressure regulator and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained for 20 h. The reactor was cooled to approximately 25° C. and depressurized and the reactor content filtered through a filter yielding a clear, slightly yellow solution of potassium tricyclohexylborohydride in THF in approximately 71% yield.

Example 9
Potassium triphenylborohydride in THF 1.94 g Potassium metal, 177.8 g dry tetrahydrofuran and 10 g triphenylborane were charged to a Parr pressure reactor equipped with a backpressure regulator and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained 16 hours. The reactor was cooled to approximately 25° C. and depressurized yielding a solution of potassium triphenylborohydride in THF (approximately 50% by $^{11}$B-NMR).

Example 10
Potassium B-isopinocampheyl-9-boratabicyclo-[3.3.1] nonane 7.27 g Potassium metal, 107 g dry tetrahydrofuran and 41.23 g (S)-B-isopinocampheyl-9-borabicyclo[3.3.1]nonane were charged to a Parr pressure reactor equipped with a backpressure regulator and a bubbler system. The mixture was heated to approximately 65° C. to melt the potassium metal and then agitated to disperse the potassium metal in the THF. The temperature was increased to 85° C.

Hydrogen gas pressure was applied to the reactor until the reactor pressure reached 50 psig. This pressure was maintained 16 hours. The reactor was cooled to approximately 25° C. and depressurized yielding a solution of potassium B-isopinocampheyl-9-boratabicyclo[3.3.1]nonane in THF (approximately 50% by $^{11}$B-NMR).

Example 11
Lithium tri-sec-butylborohydride in THF 456.85 g of potassium tri-sec-butylborohydride (1.4 molar in THF) were added to a mixture of 29.7 g LiCl in 50 ml THF at 65° C. The reaction mixture was stirred for 2–4 hours at 65° C., cooled to room temperature and then filtered. The filter cake was then washed twice with 79.1 g THF. The filtrates were combined yielding lithium tri-sec-butyl borohydride in tetrahydrofuran as a clear, pale yellow liquid (99+% pure by atomic absorption).

Example 12
Sodium tri-sec-butylborohydride in THF 8.05 g of sodium metal, 239.9 g dry THF and 66.94 g, tri-sec-butylborane, 1.14 g iron(III)chloride (FeCl$_3$) and 22.4 g napthalene were charged to a Parr pressure reactor equipped with a back pressure regulator and a bubbler system. The mixture was heated to approximately 100° C. to melt the sodium metal and then agitated to disperse the sodium metal in the THF. The temperature was increased to approximately 110° C.

Hydrogen gas pressure was applied to the reactor until the reactor pressure reached 80 psig. This pressure was maintained overnight. The reactor was cooled to approximately 25° C. and depressurized yielding a solution of sodium tri-sec-butyborohydride in THF (approximately 64% by $^{11}$B-NMR).

Example 13
Sodium tri-sec-butylborohydride in THF 8.05 g sodium metal, 239.9 g dry tetrahydrofuran, 1.14 g iron(III)chloride and 2.24 g napthalene were charged to a Parr pressure reactor equipped with a backpressure regulator (set at 95 psig) and a bubbler system. The mixture was heated to approximately 100° C. to melt the sodium metal and then agitated to disperse the sodium metal in the THF. The temperature was increased to approximately 110° C.

Hydrogen gas pressure was applied to the reactor until reactor pressure reached approximately 80 psig. This pressure was maintained overnight. The reactor was cooled to approximately 20° to 30° C. and then 66.94 g tri-sec-butylborane was added. After completion of the addition of tri-sec-butylborane, the reaction mixture was stirred for approximately one hour and then filtered through a filter. The filtrate contained the sodium tri-sec-butyl borohydride in approximately 90% yield.

Example 14
Lithium tri-sec-butylborohydride in THF 200 ml of sodium tri-sec-butylborohydride (0.9 molar in THF) were added to a mixture of 8.9 g LiCl in 23.1 ml THF at 65° C. The reaction mixture was stirred for approximately one hour at 65° C., cooled to room temperature and then filtered. The filter cake was then washed twice with 79.1 g THF. The analysis of the filtrate by $^{11}$B-NMR and atomic absorption confirmed the presence of lithium tri-sec-butylborohydride.

Example 15
Lithium tri-sec-butyl borohydride in THF (1-Step, 1-Reaction Vessel)

3.47 g Lithium metal powder, 345.0 g dry tetrahydrofuran, 1.62 g iron(III)chloride and 92.9 g tri-sec-butylborane were charged to a Parr pressure reactor equipped with a backpressure regulator (set at 95 psig) and a bubbler system. The mixture was heated to approximately 85° C.

Hydrogen gas pressure was applied to the reactor until the reactor pressure reached approximately 50 psig. This pressure was maintained overnight. The reactor was then cooled to approximately 25° C. and depressurized. The reactor content was then filtered through a filter. The filtrate contained the lithium tri-sec-butyl borohydride.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of synthesizing an alkali metal trisubstituted borohydride compound having the formula M[R$^1$R$^2$R$^3$B]H, wherein M is K, Li, Na or Cs, and R$^1$, R$^2$ and R$^3$ are, independently, an alkyl group, an aryl group, an alkoxyl group, or an aryloxyl group; the method comprising the step of reacting an alkali metal, a hydrogen donor, and a trisubstituted borane having the formula R$^1$R$^2$ R$^3$B in a single reaction vessel to product the alkali metal trisubstituted borohydride compound.

2. The method of claim 1 wherein the alkyl group is a C$_1$–C$_{12}$ alkyl group.

3. The method of claim 1 wherein the aryl group is a phenyl group or a napthyl group.

4. The method of claim 1 wherein the alkoxyl group has the formula —OR$^4$, wherein R$^4$ is a C$_1$–C$_{12}$ alkyl group.

5. The method of claim 1 wherein the aryloxyl group has the formula —OR$^5$, wherein R$^4$ is an aryl group.

6. The method of claim 1 wherein a hydrogenation catalyst is added to the reaction vessel.

7. The method of claim 6 wherein the alkali metal is lithium, the trisubstituted borane is tri-sec-butylborane and the alkali metal trisubstituted borohydride compound is lithium tri-sec-butylborohydride.

8. The method of claim 6 wherein the alkali metal is sodium, the trisubstituted borane is tri-sec-butylborane and the alkali metal trisubstituted borohydride compound is sodium tri-sec-butylborohydride.

9. The method of claim 1 wherein the alkali metal is potassium.

10. The method of claim 9 wherein no catalyst is added to the reaction vessel.

11. The method of claim 1 wherein the trisubstituted borane is tri-sec-butylborane, tricyclohexylborane, triethylborane, triphenylborane, trisiamylborane, triisopropyl borate, (S)-B-isopinocampheyl-9-borabicyclo[3.3.1]nonane or 9-isopropoxy-9-borabicyclo[3.3.1]nonane.

12. The method of claim 1 wherein the alkali metal is potassium, the trisubstituted borane is tri-sec-butylborane and the reaction takes place in a nonpolar solvent, and solid potassium tri-sec-butyl borohydride is obtained.

13. The method of claim 12 wherein the solvent is an alkane.

14. The method of claim 1 wherein the hydrogen donor is, hydrogen, deuterium, or an ether.

15. The method of claim 1 wherein the pressure in the reactor is no greater than approximately 100 psig.

16. The method of claim 1 wherein the pressure in the reactor is no greater than approximately 50 psig.

17. A method of synthesizing an alkali metal trisubstituted borohydride compound having the formula $M[R^1R^2R^3B]H$, wherein M is K, Li, Na or Cs, and $R^1$, $R^2$ and $R^3$ are, independently, an alkyl group, an aryl group, an alkoxyl group, or an aryloxyl group, the method comprising the steps of:

a. reacting an alkali metal with a hydrogen donor; and b. combining a reaction mixture of step a. with a trisubstituted borane having the formula $R^1R^2R^3B$.

18. The method of claim 17 wherein the reaction of step a. proceeds in the presence of a hydrogenation catalyst.

19. The method of claim 17 wherein the alkyl group is a $C_1$–$C_{12}$ alkyl group.

20. The method of claim 17 wherein the aryl group is a phenyl group or a napthyl group.

21. The method of claim 17 wherein the alkoxyl group has the formula —$OR^4$, wherein $R^4$ is a $C_1$–$C_{12}$ alkyl group.

22. The method of claim 17 wherein the aryloxyl group has the formula —$OR^5$, wherein $R^4$ is an aryl group.

23. The method of claim 18 wherein the alkali metal is lithium, the trisubstitued borane is tri-sec-butylborane and the alkali metal trisubstituted borohydride compound is lithium tri-sec-butylborohydride.

24. The method of claim 17 wherein the alkali metal is potassium.

25. The method of claim 24 wherein the trisubstituted borane is tri-sec-butylborane, tricyclohexylborane, triethylborane, triphenylborane, trisiamylborane, triisopropyl borate, (S)-B-isopinocampheyl-9-borabicyclo[3.3.1]nonane or 9-isopropoxy-9-borabicyclo[3.3.1]nonane.

26. The method of claim 17 wherein the alkali metal is potassium, the trisubstituted borane is tri-sec-butylborane and reactions of steps a. and b. take place in a nonpolar solvent, and solid potassium tri-sec-butylborohydride is obtained.

27. The method of claim 25 wherein the solvent is an alkane.

28. The method of claim 17 wherein the hydrogen donor is, hydrogen, deuterium, or an ether.

29. The method of claim 17 wherein the pressure in the reactor is no greater than approximately 100 psig.

30. The method of claim 17 wherein the pressure in the reactor is no greater than a proximately 50 psig.

31. The method of claim 17 wherein steps a. and b. take place in a single reaction vessel.

32. The method of claim 17 wherein the alkali metal and the trisubstituted borane are added in stoichiometric quantities.

33. A chemical composition comprising solid potassium tri-sec-butyl borohydride.

34. A method of synthesizing an alkali metal trisubstituted borohydride compound having the formula $M^1[R^1R^2R^3B]H$, wherein $M^1$ is K, Li, Na or Cs, and $R^1$, $R^2$ and $R^3$ are, independently, an alkyl group or an aryl group; the method comprising the step of reacting an alkali metal trisubstituted borohydride compound having the formula $M^2[R^1R^2R^3B]H$, wherein $M^2$ is K, Li, Na or Cs, and $M^1$ and $M^2$ are different, with a salt of $M^1$ in a solvent, wherein the salt of $M^1$ is more soluble in the solvent than a corresponding salt of $M^2$.

35. The method of claim 34, wherein $M^2$ is K or Na and $M^1$ Li.

* * * * *